(12) United States Patent
Murthy et al.

(10) Patent No.: US 9,744,156 B2
(45) Date of Patent: Aug. 29, 2017

(54) METHODS AND COMPOSITIONS FOR ENHANCED TRANSUNGUAL DELIVERY OF AR-12

(71) Applicant: Arno Therapeutics, Inc., Flemington, NJ (US)

(72) Inventors: Sathyanarayana Narasimha Murthy, Oxford, MS (US); Stefan Proniuk, Austin, TX (US)

(73) Assignee: ARNO THERAPEUTICS, INC., Flemington, NJ (US)

( * ) Notice: Subject to any disclaimer, the term of this patent is extended or adjusted under 35 U.S.C. 154(b) by 0 days.

(21) Appl. No.: 15/237,435

(22) Filed: Aug. 15, 2016

(65) Prior Publication Data

US 2017/0049748 A1 Feb. 23, 2017

Related U.S. Application Data

(60) Provisional application No. 62/206,188, filed on Aug. 17, 2015.

(51) Int. Cl.
| | |
|---|---|
| *A61K 31/415* | (2006.01) |
| *A61K 47/18* | (2017.01) |
| *A61K 47/10* | (2017.01) |
| *A61K 9/00* | (2006.01) |

(52) U.S. Cl.
CPC .......... *A61K 31/415* (2013.01); *A61K 9/0014* (2013.01); *A61K 47/10* (2013.01); *A61K 47/18* (2013.01)

(58) Field of Classification Search
CPC .................................................. C07D 231/12
USPC ......................................................... 514/406
See application file for complete search history.

(56) References Cited

U.S. PATENT DOCUMENTS

| | | |
|---|---|---|
| 8,889,680 B2 | 11/2014 | Krysan et al. |
| 2012/0214874 A1 | 8/2012 | Buyuktimkin et al. |
| 2012/0309843 A1 | 12/2012 | Buyuktimkin et al. |
| 2016/0199351 A1* | 7/2016 | Rappleye et al. ..... A61K 45/06 424/450 |

OTHER PUBLICATIONS

Nair, et al., "Effect of Polyethylene Glycols on the Trans-Ungual Delivery of Terbinafine," Current Drug Delivery, 2010, vol. 7, No. 5, pp. 407-414.
Akhtar, et al., "Onychromycosis: Potential of Nail Lacquers in Transungual Delivery of Antifungals," Scientifica, 2016, p. 4.
International Search Report and Written Opinion of International PCT Application No. PCT/US2016/047087 dated Nov. 18, 2016.

* cited by examiner

*Primary Examiner* — Raymond Henley, III
(74) *Attorney, Agent, or Firm* — VLP Law Group LLP; Jeremy A. Cubert

(57) ABSTRACT

Methods and compositions for enhancing transungual delivery of AR-12 comprising administering AR-12 and permeation enhancers are provided.

12 Claims, 2 Drawing Sheets

METHODS AND COMPOSITIONS FOR ENHANCED TRANSUNGUAL DELIVERY OF AR-12

This application claims priority to U.S. Provisional Patent Application Ser. No. 62/206,188, filed Aug. 17, 2015. The above referenced application is incorporated herein by reference as if restated in full

BACKGROUND

*Trichophyton* is a filamentous fungus which grows as hyphae in and on host tissues. The fungus is acquired by contact with material such as shed skin scales contaminated with *Trichophyton* hyphae and hyphal elements. The *Trichophyton* hyphae produce keratinases which enable them to use keratin as a nutrient source. *Trichophyton* colonizes the keratinized stratum corneum of the skin presenting a chronic source of continued infection. Although direct invasion of living tissue is rare, the presence of the *Trichophyton* fungus induces inflammatory responses in the surrounding tissue. Disease conditions caused by *Trichophyton* include infections of the skin (e.g., tinea pedis [athletes foot] and tinea corporis [ringworm]), of the nails, and nail bed (tinea unguium or onychomycosis). Fungal infection of the nails and nail bed is of particular concern, because fungi can penetrate deep into the nail plate, nail bed, and nail matrix causing long term, chronic infections that are difficult to treat.

Current treatments for fungal pathogens include clotrimazole, econazole, ketoconazole, miconazole, tioconazole, fluconazole, posaconazole, itraconazole, voriconazole, isavuconazonium, terbinafine, nystatin, amorolfine, griseofulvin, caspofungin, micafungin, anidulafungin, tevaborole, efinaconazole, amphotericin B deoxycholate and liposomal amphotericin B, and are typically provided topically, orally, or intravenously. Side-effects include liver damage, allergic reactions, and hormonal effects. In particular, triazole-based drugs have significant host side-effects such as reversible increases in hepatic enzymes, nausea, vomiting, diarrhea, abdominal pain, constipation, dyspepsia, allergic reactions such as pruritus, rash, urticarial, angioedema, and hepatitis after prolonged use.

AR-12 (a.k.a. OSU-03012) has been previously shown to exhibit anti-tumor, antifungal, and anti-bacterial activity. It is thought that AR-12 induces autophagy of cells harboring intracellular microbes.

SUMMARY

Aspects described herein provide methods and compositions for enhancing transungual penetration of AR-12.

One aspect provides methods of administering AR-12 to a nail by administering a composition comprising AR-12 and a permeation enhancer to the nail in an amount sufficient to achieve an AR-12 concentration of at least about 0.02 μg/mg in the nail plate.

With respect to this aspect, the permeation enhancer is selected from the group consisting of dexpanthenol and polyethylene glycol 400. In a further aspect, the permeation enhancer comprises dexpanthenol and polyethylene glycol 400.

Yet another aspect provides methods of administering AR-12 to a nail by administering a composition comprising AR-12 and a permeation enhancer to a nail in an amount sufficient to achieve a cumulative amount of AR-12 permeated across the nail plate of at least about 3 μg/cm².

With respect to this aspect, the permeation enhancer is selected from the group consisting of dexpanthenol and polyethylene glycol 400. In a further aspect, the permeation enhancer comprises dexpanthenol and polyethylene glycol 400.

Further aspects provide compositions comprising AR-12 and dexpanthenol. In one aspect the concentration of dexpanthenol in the composition is at least about 5%.

Further aspects provide compositions comprising AR-12 and polyethylene glycol 400. In one aspect the concentration of polyethylene glycol 400 in the composition is at least about 5%.

Yet another aspect provides compositions comprising AR-12, dexpanthenol, and polyethylene glycol 400.

BRIEF DESCRIPTION OF THE DRAWINGS

The feature and nature of the present disclosure will become more apparent from the detailed description set forth below when taken in conjunction with the accompanying drawings.

DETAILED DESCRIPTION

Figure 1:
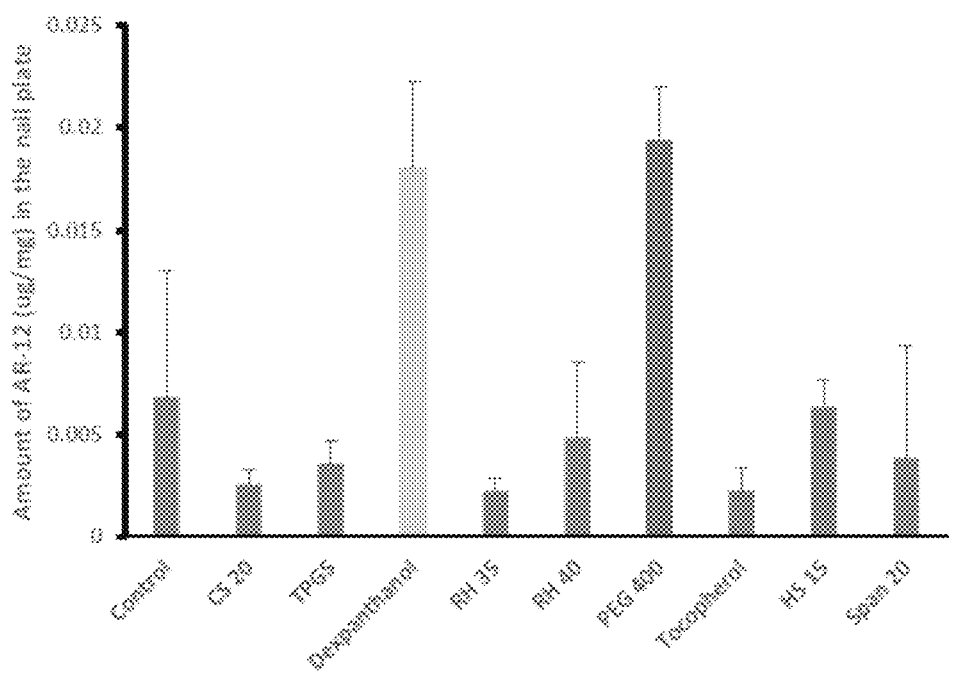
FIG. 1 shows the results of an exemplary study of the amount of AR-12 accumulated in the nail plate after AR-12 and the indicated permeation enhancer or a control without a permeation enhancer is administered to cadaver nails for 24 hours.

The disclosed methods, compositions, and devices below may be described both generally as well as specifically. It should be noted that when the description is specific to an aspect, that aspect should in no way limit the scope of the methods. All references cited herein are hereby incorporated by reference in their entirety.

The term "nail" refers to the finger or toe nail of a mammal and includes several parts including (1) the nail plate (e.g., the visible part of the nail), (2) the nail bed (e.g., the skin under the nail plate, (3) the lunula (e.g., the crescent shaped portion below the nail plate) and (4) the nail matrix (from where the nail plate grows). The nail is highly susceptible to fungal infection due to exposure to moisture and environments where fungal infections can be acquired (e.g., bathrooms, gyms, showers etc.). *Trichophyton* infections of the nail can lead to discoloration and development of brittle, thickened nails. In addition, the infection could spread to other parts of the body with serious consequences—especially for patients with other conditions such as diabetes. In some cases, these infections can lead to complications resulting in amputation. Improved treatments for nail fungal infections are needed.

As used herein, "concentration" refers to a concentration of a drug (e.g., AR-12) in the nail of the host. In one aspect, the nail is infected with a fungus.

As used herein, the term "administer" or "administered" refers to applying or prescribing an active ingredient to treat a host or patient in need of treatment. The host can be a mammal (e.g., humans, dogs, cats, horses, and cows).

Methods described herein provide for administering a composition comprising AR-12 and a permeation enhancer to the nail. The term "permeation enhancer" refers to a chemical compound capable of improving the rate and extent of delivery of a drug to the site of treatment and time the drug remains at the site of treatment. For example, permeation enhancement of the drug can be measured by measuring the amount of drug penetrated into and across the tissue or the depth of penetration of drug into the tissue.

Permeation enhancers include CS20 (Polyoxyl 20 Cetostearyl Ether), TPGS (vitamin E polyethylene glycol succinate), Dexpanthenol, RH 35 (poly oxyl 35 castor oil), RH 40 (polyoxyl 40 hydrogenated castor oil), PEG 400 (polyethylene glycol 400), Tocopherol (D-alpha-tocopherol polyethylene glycol 1000 succinate), HS15 (polyoxyl 15 hydroxystearate), and Span 20 (sorbitan monolaurate). Combinations of permeation enhancers may also be used to further enhance drug delivery (e.g., dexpanthenol and polyethylene glycol). In one aspect, the concentration of permeation enhancer in the compositions described herein is at least about 5%. In another aspect, the concentration of permeation enhancer in the compositions described herein is about 0.05% to about 50%.

As described herein, human nail plates were used for the screening of penetration enhancers. Nail clippings were placed in the 5% w/v drug solution prepared in ethanol with or without enhancers for 24 hours (h). The nail plates were washed five times with ethanol and water. Each nail clipping was solubilized in 2 ml of 1M sodium hydroxide solution by subjecting on the shaker at 37° C. for 24 h. Then, 0.4 ml of 5M hydrochloric acid was added to neutralize the sodium hydroxide solution. Drug was extracted by adding 2 ml of ethyl acetate to the final neutral solution. The ethyl acetate layer was collected and evaporated using nitrogen gas. The residue of AR-12 was dissolved in ethanol prior to analysis. Table 1 below summarizes the exemplary permeation enhancers used and their percentage (w/v) to the drug in each sample.

TABLE 1

| Name of enhancer | Percentage |
| --- | --- |
| Control | No enhancer |
| CS20 | 5% CS20 |
| TPGS | 5% TPGS |
| Dexpanthenol | 5% dexpanthenol |
| RH 35 | 5% RH 35 |
| RH 40 | 5% RH 40 |
| PEG 400 | 5% PEG 400 |
| Tocopherol | 5% Tocopherol |
| HS 15 | 5% HS 15 |
| Span 20 | 5% Span 20 |

As described herein, dexpanthenol and PEG-400 are preferred enhancers for the trans-ungual delivery of AR-12 (FIG. 1). To further explore these results, in vitro permeability studies across cadaver nail plate were performed.

The permeation study was performed in Franz diffusion cells fitted with nail adapter. The finger nails (from all fingers except the little finger) of human cadavers obtained from ScienceCare were used for the transport studies. The nail plates were cleaned with water, and nail plates of 400-450 micron thickness were selected and visually inspected for presence of any cracks or pores. After mounting on the diffusion cell, the donor as well as the receiver compartments were filled with phosphate buffered saline (1:1 ethanol:PBS, pH 7.4) and allowed to equilibrate for 3 hours for complete hydration of the nail plate. The electrical resistivity across the nail plate was measured prior to removal of the buffer to check the intactness of the nail plate after hydration.

The permeation testing was performed using modified Franz diffusion cell. The cell consisted of two compartments: a (1) a donor compartment for placing the drug solution/formulation and (2) a receiver compartment containing the buffer in which the drug diffuses. A nail holder is placed between the two compartments. The nail holder is curved to accommodate the contour of nail plate and secures the nail between the upper and lower part of the holder.

The donor compartment was filled with 500 microliters of drug solution (50 mg/ml) prepared in ethyl alcohol. For the control sample, no enhancer was incorporated. In the test cells, the enhancer was incorporated (5% PEG or 5% dexpanthenol or both). The donor compartment was covered with parafilm to minimize the loss of solvent. The drug solution was removed every 2 hours, the donor compartment was washed two times with 500 microliters of alcohol, and fresh drug solution (50 mg/ml) was placed in the donor compartment. The receiver compartment was filled with 50% alcohol in PBS and it was continuously stirred at 600 rpm. The receiver compartment fluid was sampled at predetermined time points (e.g., 0, 12, 24, 36, 48, 60, 72, 84, 96, 108, 120, 132, 144, 156, 192, 204, 216 minutes) and the amount of drug permeated across the nail plate was quantitated by high pressure liquid chromatography.

Figure 2:
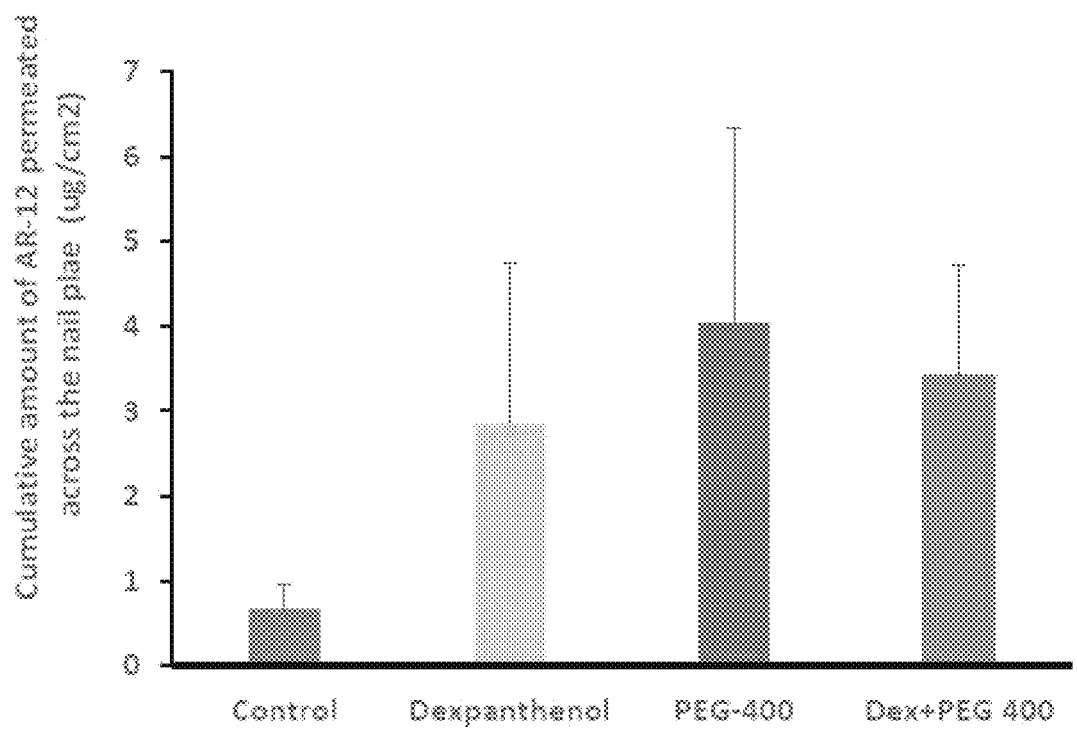
FIG. 2 shows the results of an exemplary study of the cumulative amount of AR-12 permeated across the nail plate after AR-12 and the indicated permeation enhancer(s) and a control without a permeation enhancer is administered to cadaver nails after a one week period.

For this example, the amount of drug permeated in a one week period across the nail plate in control was 658±306 ng. The permeation flux was enhanced significantly by four fold in case of dexpanthenol and about six fold in case of PEG-400 (FIG. 2). Combination of the two enhancers did not lead to synergistic effect indicating that both the enhancers could be working by similar mechanisms.

As used herein, the term AR-12, refers to, ($C_{26}H_{19}F_3N_4O$ and 2-amino-N-(4-(5-(phenanthren-2-yl)-3-(trifluoromethyl)-1H-pyrazol-1-yl)phenyl)acetamide)), having the following structure:

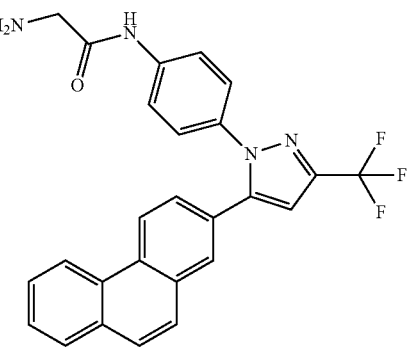

The term "AR-12" also includes, for example, analogs of AR-12 (e.g., the compounds described in U.S. Pat. Nos. 7,576,116, 8,546,441, 8,541,460, 8,039,502, and 8,080,574 hereby incorporated by reference in their entirety).

AR-12 described herein can be topically applied with respect to treating a nail fungus infection. Dosage forms known to those of skill in the art are suitable for delivery of AR-12 are described herein.

For example, AR-12 can be formulated into suitable topical pharmaceutical preparations such as creams, gels, or solutions. AR-12 can be formulated into pharmaceutical compositions using techniques and procedures well known in the art.

In one aspect, about 0.1 to 1000 mg, about 5 to about 100 mg, or about 10 to about 50 mg of the AR-12, or a physiologically acceptable salt or ester can be compounded with a physiologically acceptable vehicle, carrier, excipient, emollients, diluents, solvents, polymers for viscosity adjustment, preservatives, stabilizer, etc., for use in a multiple use container as called for by accepted pharmaceutical practice. The amount of active substance in compositions or preparations comprising AR-12 is such that a suitable dosage in the range indicated is obtained.

In another aspect, the compositions can be formulated for use in a multiple use container, each dosage containing from about 1 to about 1000 mg, about 1 to about 500 mg, or about 10 to about 100 mg of the active ingredient. The term "multiple use container" refers to a container that is capable of dispensing multiple dosages for human subjects and other mammals, each dosage containing a predetermined quantity of active material calculated to produce the desired therapeutic effect, in association with a suitable pharmaceutical excipient when used according to the directions. In another aspect, a single-dose container can be used (e.g., patch).

In one aspect, one or more of AR-12 is mixed with a suitable pharmaceutically acceptable carrier to form compositions. Upon mixing or addition of the compound(s), the resulting mixture may be a cream, gel, solution, suspension, emulsion, nanoparticles or the like. Liposomal or niosomal or any vesicular form suspensions may also be used as pharmaceutically acceptable carriers. These may be prepared according to methods known to those skilled in the art. The form of the resulting mixture depends upon a number of factors, including the intended mode of administration and the solubility of the compound in the selected carrier or vehicle. In one aspect, the effective concentration is sufficient for lessening or ameliorating at least one symptom of the disease, disorder, or condition treated and may be empirically determined.

Pharmaceutical carriers or vehicles suitable for administration of AR-12 described herein include any such carriers suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

In another aspect, if AR-12 exhibits insufficient solubility, methods for solubilizing may be used. Such methods are known and include, but are not limited to, using co-solvents such as dimethylsulfoxide (DMSO), buffers, using surfactants such as TWEEN, and dissolution in aqueous sodium bicarbonate. Derivatives of the compounds, such as salts or prodrugs, may also be used in formulating effective pharmaceutical compositions.

The concentration of the compound is effective for delivery of an amount upon administration that lessens or ameliorates at least one symptom of the disorder for which the compound is administered. Typically, the compositions are formulated for single and multiple dosage administration.

In another aspect, AR-12 as described herein may be prepared with carriers that protect them against rapid elimination from the body, such as sustain-release point formulations or coatings. Such carriers include controlled release formulations, such as, but not limited to, microencapsulated delivery systems. The active compound can be included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

In another aspect, AR-12 and compositions described herein can be enclosed in multiple or single dose containers. The enclosed compounds and compositions can be provided in kits, for example, including component parts that can be assembled for use. For example, AR-12 in lyophilized form and a suitable diluent may be provided as separated components for combination prior to use. A kit may include AR-12 and a second therapeutic agent for co-administration. AR-12 and second therapeutic agent may be provided as separate component parts. A kit may include a plurality of containers, each container holding one or more unit dose of AR-12 described herein. In one aspect, the containers can be adapted for the desired mode of administration, including, but not limited to topical administration (e.g., patches, medipads, gels, suspensions, creams, and the like.

The concentration of AR-12 in the pharmaceutical composition will depend on absorption, inactivation, and excretion rates of the active compound, the dosage schedule, and amount administered as well as other factors known to those of skill in the art.

In another aspect, the active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The active materials can also be mixed with other active materials that do not impair the desired action, or with materials that supplement the desired action. AR-12 can be used, for example, in combination with an antibiotic, antifungal, pain reliever, or cosmetic.

In one aspect, solutions or suspensions used for topical application can include any of the following components: a diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, alcohols, polyethylene glycol, glycerin, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose.

In another aspect, AR-12 may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The dosage forms can be administered to the patient 1, 2, 3, or 4 times daily. AR-12 as described herein can be administered either three or fewer times, or even once or twice daily.

The terms "therapeutically effective amount" and "therapeutically effective period of time" are used to denote treatments at dosages and for periods of time effective to reduce nail fungal growth at a sufficient dosage to attain a Minimum Inhibitory Concentration (MIC) of the compounds from about 0.1 µM to about 20 µM. For localized administration, much lower concentrations than this can be effective, and much higher concentrations may be tolerated. One of skill in the art will appreciate that such therapeutic effect resulting in a lower effective concentration of AR-12 may vary considerably depending on the tissue, organ, or the particular animal or patient to be treated. It is also understood that while a patient may be started at one dose, that dose may be varied overtime as the patient's condition changes.

It should be apparent to one skilled in the art that the exact dosage and frequency of administration will depend on the particular compounds employed in the methods of the disclosure administered, the particular condition being treated, the severity of the condition being treated, the age, weight, nail thickness, extent of hyperkeratinization, dystrophy, nail porosity, general physical condition of the particular patient, and other medications the individual may be taking.

Not every element described herein is required. Indeed, a person of skill in the art will find numerous additional uses of and variations to the methods described herein, which the inventors intend to be limited only by the claims. All references cited herein are incorporated by reference in their entirety.

What is claimed as new and desired to be protected by Letters Patent of the United States is:

1. A method of administering AR-12 to a nail comprising administering a composition comprising AR-12 and a permeation enhancer to a nail in an amount sufficient to achieve an AR-12 concentration of at least about 0.02 µg/mg in the nail plate.

2. The method of claim 1, wherein the permeation enhancer is selected from the group consisting of dexpanthenol and polyethylene glycol 400.

3. The method of claim 2, wherein the permeation enhancer comprises dexpanthenol and polyethylene glycol 400.

4. A method of administering AR-12 to a nail comprising administering a composition comprising AR-12 and a permeation enhancer to a nail in an amount sufficient to achieve a cumulative amount of AR-12 permeated across the nail plate of at least about 3 µg/cm2.

5. The method of claim 4, wherein the permeation enhancer is selected from the group consisting of dexpanthenol and polyethylene glycol 400.

6. The method of claim 4, wherein the permeation enhancer comprises dexpanthenol and polyethylene glycol 400.

7. A composition comprising AR-12 and dexpanthenol.

8. A composition comprising AR-12 polyethylene glycol 400.

9. A composition comprising AR-12 and dexpanthenol and polyethylene glycol 400.

10. The composition of claim 7, wherein the concentration of dexpanthenol in the composition is about 5%.

11. The composition of claim 8, wherein the concentration of polyethylene glycol in the composition is about 5%.

12. The composition of claim 9, wherein the concentration of each of dexpanthenol and polyethylene glycol in the composition is about 5%.

* * * * *

UNITED STATES PATENT AND TRADEMARK OFFICE
CERTIFICATE OF CORRECTION

PATENT NO. : 9,744,156 B2
APPLICATION NO. : 15/237435
DATED : August 29, 2017
INVENTOR(S) : Sathyanarayana Narasimha Murthy Page 1 of 1

It is certified that error appears in the above-identified patent and that said Letters Patent is hereby corrected as shown below:

In the Specification

Column 1, Lines 5-8 replace the Government Support Clause with:
--This invention was made with government support under grant number CA094829 awarded by the National Institutes of Health and grant number DAMD17-02-1-0117 awarded by the United States Army Medical Research and Materiel Command. The government has certain rights in the invention.--

Signed and Sealed this
Thirteenth Day of October, 2020

Andrei Iancu
*Director of the United States Patent and Trademark Office*